United States Patent [19]

Olsen et al.

[11] Patent Number: 5,051,259
[45] Date of Patent: Sep. 24, 1991

[54] SKIN BARRIER PRODUCT WITH DISCONTINUOUS ADHESIVE LAYER

[75] Inventors: Hans Olsen, Bronshoj; Finn Poulsen, Vaerlose; Peter Samuelsen, Rungsted Kyst, all of Denmark

[73] Assignee: Coloplast A/S, Espergerde, Denmark

[21] Appl. No.: 382,660

[22] PCT Filed: Dec. 5, 1988

[86] PCT No.: PCT/DK88/00202
§ 371 Date: Oct. 10, 1989
§ 102(e) Date: Oct. 10, 1989

[87] PCT Pub. No.: WO89/05619
PCT Pub. Date: Jun. 29, 1989

[30] Foreign Application Priority Data

Dec. 15, 1987 [DK] Denmark .......................... 6571/87

[51] Int. Cl.⁵ .................. A61F 13/02; A61F 5/443; B32B 3/10
[52] U.S. Cl. .................. 424/443; 424/447; 424/448; 604/307; 604/344; 604/336; 604/338; 428/913; 428/107; 428/195; 428/343; 428/349; 428/351; 428/355; 428/507; 428/479.3; 428/131; 428/108; 428/37; 428/109; 428/906; 428/110; 428/114; 428/192; 428/196; 428/64; 428/65; 428/66; 428/304.4; 428/317.1; 428/317.3; 428/317.5; 428/317.7; 428/457; 428/542.8

[58] Field of Search ............... 428/913, 107, 195, 343, 428/349, 351, 355, 507, 479.3, 131, 108, 37, 109, 906, 110, 114, 192, 196, 64, 65, 66, 308.4, 317.1, 317.3, 317.5, 317.7, 457, 542.8; 424/443, 447, 448; 604/307, 344, 336, 338

[56] References Cited

U.S. PATENT DOCUMENTS

| | | | |
|---|---|---|---|
| 2,614,963 | 10/1952 | Elson | 604/307 |
| 3,081,771 | 4/1961 | Lee | 604/344 |
| 3,342,183 | 9/1967 | Edenbaum | 424/448 X |
| 3,734,097 | 5/1973 | Zattaroni | 424/448 X |
| 3,885,559 | 5/1975 | Economou | 128/156 |
| 4,061,820 | 12/1977 | Magid et al. | 428/195 X |
| 4,219,019 | 8/1980 | Coates | 128/156 |
| 4,231,369 | 11/1980 | Sorensen et al. | 604/336 |
| 4,367,732 | 1/1983 | Poulsen et al. | 604/307 |
| 4,551,490 | 11/1985 | Nozle et al. | 604/344 X |
| 4,743,249 | 5/1988 | Lovelund | 604/307 X |
| 4,750,482 | 6/1988 | Sieverding | 128/156 |

FOREIGN PATENT DOCUMENTS

| | | | |
|---|---|---|---|
| 56-02909 | 1/1981 | Japan | 424/448 |
| 6804 | of 1888 | United Kingdom | 604/307 |
| 20808 | of 1897 | United Kingdom | 604/307 |
| 463 | of 1904 | United Kingdom | 604/307 |

Primary Examiner—Ellis P. Robinson
Assistant Examiner—William P. Watkins, III
Attorney, Agent, or Firm—Armstrong, Nikaido, Marmelstein, Kubovcik & Murray

[57] ABSTRACT

An adhesive, flat skin barrier product for use as semi-manufacture in the production of, a.o., dressings, wound-care devices, electrodes and fastening means for ostomy equipment and catheters, consists of alternating zones of material of at least two different kinds (26,28,30) at least one of which is a skinfriendly self-adhesive material. The zones are parallel and extend in a direction usually at right angles to the main surfaces of the product. The zones may for instance be parallel strips, co-axial rings, co-wound Archimedean spirals or short strands.

The skin barrier product offers the advantage that in a simple way it may be produced to comprise, besides the sealing material itself, other components for special purposes, e.g. having contents of antiseptics, medicaments or others biologically active substances of liquid-transporting or electrically conductive structures.

28 Claims, 3 Drawing Sheets

SKIN BARRIER PRODUCT WITH DISCONTINUOUS ADHESIVE LAYER

FIELD AND BACKGROUND OF THE INVENTION

The present invention relates to an adhesive, flexible flat skin barrier product for use as a semi-manufacture in the production of dressings, skin and wound care devices, fastening means for dressings, ostomy equipment, wound drains and catheters, e.g. for incontinence equipment for men and for similar applications, and for use in electrodes for application to the skin.

A large number of flexible skin barrier products of this general type are known, and many of them have as a main component a sealing material comprising a continuous phase containing an adhesive and for instance being built from an elastomer, an emulsifier for the elastomer, a resin promoting the adhesive capacity and optionally an oil-based extender as well as an antioxidant. In this there is in many cases dispersed a discontinuous phase comprising one or more water-soluble or water-swellable hydrocolloids, starch derivatives or cellulose derivatives or hydrophilic polymers.

Examples hereof are those known from U.S. Pat. Nos. 4,231,369 and 4,367,732. They consist of a continuous phase comprising a physically cross-linked elastomer in the form of one or more styrene-olefin-styrene block copolymers or ethylene-propylene block copolymers, a hydrocarbon tackifier in the form of a polymer or copolymer from cyclopentadiene, dicyclopentadiene, α-pinene and/or β-pinene, an antioxidant and optionally a liquid paraffin as an emulsifier; and in this a discontinuous phase comprising one or more water-swellable hydrocolloids, preferably gum guar and/or sodium carboxymethyl cellulose. Known skin barriers may also contain other elastomers, e.g. natural rubber, synthetic resins of a similar nature as natural rubber and silicone rubbers. As adhesive material and structure-forming component in skin barriers polyisobutylene of a suitable molecular weight distribution is also frequently used, e.g. as stated in U.S. Pat. No. 3,339,546. In principle, all known skin-friendly self-adhesive sealants may be present in the skin barrier product according to the invention.

In the majority of the known skin barriers the composition thereof is substantially uniform over the whole of the width and length dimension (hereinafter sometimes together called the surface dimension, i.e. seen as passing from one edge to an opposite edge thereof), incidentally as a rule also in the thickness dimension, as regards the adhesive composition. This is often an advantage but in a number of instances varying properties in the surface direction may be desirable, for instance in such a way that regions or portions of adhesive material forming an angle to the flat surfaces of the product alternate with regions or portions of another kind equally forming an angle to the surfaces of the skin barrier product, e.g. made of another kind of adhesive material, of less adhesive or of non-adhesive material; or materials having more or less pronounced barrier properties, having liquid-conducting or electrically conducting properties, materials containing wound-healing substances or medicaments, or absorbing materials.

U.S. Pat. No. 3,885,559 discloses a process for the reduction of pain in the removal of adhesive tapes or bandages. This is achieved by using an adhesive tape or bandage comprising a flexible backing with an adhesive portion distributed and adhered thereon in the form of adhesive layers alternately spaced with regions of lesser or even no adhesiveness. The backing is needed to hold the regions assembled, and the individual regions do not extend through the entire thickness of the product, viz. because of the backing.

European published Patent Application No. 134,437 A1 discloses a flexible magnetic foil for therapeutic purposes. It has a flexible rubber-like foil in which permanent magnetic ferrites have been embedded, whereby the active surface of the foil has been magnetized with poles having alternating polarity. In order to attach the foil to the skin of a patient, it is provided with self-adhesive coating which is tolerable to the skin. Thus, no kind of material extends through the entire thickness of the product.

SUMMARY OF THE INVENTION

It is the object of the invention to provide a semi-manufacture skin barrier product with properties changing in the width and/or length dimension so as to suit varying needs with one product not needing some uniform cover layer or backing unless the ultimate use of the semi-manufacture calls for the application of such a uniform layer on a surface of the product. According to the invention this is achieved if the product consists of a number of alternating zones of material of at least two different kinds, at least one kind of zone consisting of a skin-friendly self-adhesive material, the zones of material extending substantially parallelly through the entire thickness of the product in a direction intersecting its flat surfaces. Preferably the zones are substantially at right angles to the flat surfaces of the product and hence are parallel to the edges. All the kinds of material present in the product have to be substantially non-irritating to skin or mucous membranes and must also be substantially non-allergenic.

According to the invention at least one kind of zone consists of a self-adhesive material of the kind which comprises a continuous phase containing a self-adhesive elastomer mass and one or more water-soluble or water-swellable hydrocolloids substantially evenly dispersed as a discontinuous phase in the continuous phase. The self-adhesive sealing agent may thus advantageously be one of the kinds described in the abovementioned U.S. Pat. Nos. 4,231,369 and 4,367,732 and which in the continuous phase also comprise an emulsifier for the elastomer and normally an antioxidant.

The self-adhesive material or one of them may, however, have no contents of hydrocolloid and, e.g., be based on styrene-isoprene-styrene block copolymers, polyisobutylenes, polyvinylether or polyacrylates, polymethacrylates or copolymers thereof.

The skin barrier product preferably has the same thickness as known skin barriers, for instance 0.5–2 mm.

DETAILED EXPLANATION OF THE INVENTION

The various zones of material may be grouped in various ways.

In principle, thus, one or more zones may be entirely surrounded at all edges by one or more other zones, said other zones being of mutually different or identical materials. The geometrical arrangement may vary widely. Thus, as seen from the surface, one zone of one material may form an "island" in a matrix formed by another material; or a plurality of zones of the same material or different materials may form such islands in the matrix. Also, a plurality of thin platelets made of materials of two or more kinds and having irregular or regular shapes may be joined together so as to fill up the semi-manufacture.

According to another variant, two or more kinds of material are spirally wound together to form (two or more) neighbouring zones each substantially in the shape of an Archimedean spiral which may, however be more or less deformed. Such a product may be formed by stacking sheets or lengths, each having a constant thickness, of the desired materials, rolling the stack as one rolls a carpet and slicing the roll thus formed substantially perpendicularly to its axis.

In a further geometrical arrangement of the product according to the invention, the zones of material, seen from the surface of the product, are rectilinear, curved or wavy, substantially parallel and all extend from one edge of the product to another. It will be understood that each individual zone, be it rectilinear, curved or wavy, has a substantially constant width, i.e. that its edges, bordering a neighbouring zone or the outer world, are substantially equidistant.

A variant of this embodiment is one in which all of the zones form a closed curve, e.g. a circle or an elliptic curve, seen from the surface of the product. In that case the zones are cylinders of, for instance, a length of 0.5-2 mm, a central cylinder being in its entirety surrounded by one or more other and larger cylinders. Any two adjacent zones or cylinders consist of different materials. Such cylinders may be deformed.

A further variant is one in which the zones of material, seen from the surface of the product, are rectilinear, curved or wavy, substantially parallel and all extend from one edge of the product to another, at least one such zone having a function other than an adhesive function. Any zone having a function other than an adhesive function may well have, but need not have, that other function in addition to an adhesive function. For example a medicament or some liquid-transported structure may be embedded in an adhesive material.

Thus, in the present product the zones may be mainly parallel or co-axial alternating strips of identical or different thicknesses. In that case the product is a sort of laminate the layers of which are quite short and upright or at least form an angle to the main faces of the product. Preferably the strips may have a thickness of for instance 0.5-2 mm, whereby they are easily produced by slicing from a roll or a stack of layers of a usual skin barrier, alternating with layers of a different material. The zones may, however, also be thicker, especially in annular semi-manufactures of the kind in question, for instance 1-5 cm. In this case the skin barrier product may for instance be produced by extrusion, a process which may also be used in the production of a product having narrow zones, and subsequent slicing into thin sheets.

According to the invention at least one of the kinds of zones may be made of a material hampering or preventing migration of matter to and from adjacent self-adhesive zones. In other words it is a question of a more or less efficient barrier zone. These barrier zones may be of several different kinds and their presence does not exclude the presence of zones of quite another kind in the product.

This embodiment notably has importance in cases where zones of the self-adhesive sealing agent alternate with zones of another kind and it is wanted to prevent migration of matter from or into said zones of another kind. At least one of the kinds of zones may consist of a material hampering or preventing passage of aqueous liquids to adjacent hydrocolloid-containing self-adhesive materials.

The zones hampering or impeding migration of matter may for instance be films or foils of plastic or metal. Such barrier foils or films may for instance have a thickness of 10-100 μm and for instance consist of polyolefins, polyester, poyvinylchloride, aluminium or laminates thereof.

The zones hampering or preventing migration of matter could alternatively consist of a material which is ductile under the influence of low forces and also more or less hydrophobic and containing a self-adhesive elastomer mass, but no hydrocolloid. A main function of self-adhesive skin barriers containing hydrocolloid is to absorb sweat and/or wound exudates while retaining their adhesive capacity. Due to the absorption capacity thereof, such skin barrier product may, however, unwantedly absorb liquid from the edges, for instance water from bathing or secretion from stomas in case of its application for fastening ostomy equipment. When it comprises a material hampering migration of matter and especially a material hampering migration of water, the movement of the water across the edges of the zones of the skin barrier product (a movement parallel to its flat surfaces) will become very slow and the product will retain its adhesive capacity for a long period of time and thus obtain an increased life time. When the adhesive material without or poor in colloids is ductile under the influence of low forces, it will keep up with the thickness increase of the product and thereby still form a barrier against unintentionally being decomposed by water from the edges.

Since moreover materials of the kind in question may be composed in a manner so as to absorb water to a certain degree, but substantially slower than does the hydrocolloid-containing adhesive, it will be able to keep up with even very considerable increases in volume caused by the absorption of liquid.

Although the zone hampering migration of matter generally does not contain hydrocolloid, it is possible that zones of adhesive material of the kind in question and having a high content of hydrocolloid alternate with zones having a lower content of hydrocolloid instead of zones entirely devoid of hydrocolloid.

In another grouping of the zones of material they may in accordance with the invention be strands of identical or different cross-sectional shapes and sizes and substantially fill up the product. The lengths of the strands are normally the thickness of the product so that they are at right angles to the main surfaces thereof, but they may also be longer and thus be at an oblique angle to the main surfaces of the product and the edges thereof.

The strands may have any regular or irregular cross-section, but should fill up the product so that there will be no air ducts where they abut on each other. They may be prismatic and thereby in a simple manner fulfil the requirement for filling up the product if their cross-sections are either identical equilateral triangles, squares or regular hexagons. Normally they will, however, be round strands. A skin barrier product having its zones in the form of strands may be produced by co-extrusion of for instance prismatic, circular or oval, long, parallel strands of the materials in question, and subsequent slicing of the composite strand thus formed into thin pads. If the cross-sections of the strands do not by themselves ensure the complete filling up of the cross-sectional area of the product formed, one may after the extrusion but before the slicing press the single strands together into a composite strand, for instance by passing them through a slightly funnel-shaped compressing device.

At another grouping of the zones of material a number of strands are distributed evenly or unevenly in a strand of a self-adhesive material of the kind comprising a continuous phase containing a self-adhesive elastomer mass and a water-soluble or water-swellable hydrocolloid dispersed therein as a discontinuous phase, said latter strand filling up the interspaces between the former. The distribution may possibly also be the opposite: single strands of an adhesive material as mentioned, distributed in a larger strand surrounding all of them and forming a sort of matrix for them.

In the embodiment having the single strands distributed in a surrounding strand there may be strands of various kinds, i.e. strands of mutually different kinds, for instance the kinds referred to later in this specification.

The skin barrier product according to the invention may advantageously be in the form of an annular pad for affixing drains, ostomy pouches or other equipment, in which case according to the invention the alternating zones of material may be substantially co-axially cylindrical or form an Archimedean spiral, and the product may be provided with a central aperture. Further, the product may be provided on both the inner edge and the outer edge with a water-impermeable barrier layer, such as e.g. a film or foil of plastic or metal or a laminate thereof, or of a self-adhesive elastomer mass free from hydrocolloid or poor in hydrocolloid. It is thereby attained that water from the outer edge or secretion from stomas from the inner edge only slowly penetrate into the adhesive ring whereby the lifetime thereof will be substantially increased.

Such products may be produced in a far more economic way than current annular pads, which are manufactured by punching from sheets or lengths, thus causing a considerable waste of material. In contradistinction hereto an annular product as just mentioned may be manufactured by co-extrusion of materials for the zones to form a hollow cylinder having co-axial layers of material and subsequent slicing of the cylinder thus formed; or by spirally coiling assembled lengths of the materials and subsequent slicing of the hollow roll thus formed.

It is observed that by the expression "annular" reference is made to any embodiment of the product having a defined outer delimitation and a central or eccentric aperture suitable for engaging a drain or a stoma. The aperture needs not be circular but most frequently is. The outer shape may be circular, elliptic or polygonal, e.g. quadrangular, or have any other desired shape. Even products having an outer shape differing from that of the circle may be produced in the manner described above, most conveniently by performing a suitable deformation before the hollow cylinder or roll is sliced; a desired shape of the aperture may be maintained by means of a mandrel which is removed successively as the slicing proceeds.

An annular product may conveniently comprise zones that hamper or prevent migration of matter or contain a self-adhesive elastomer mass free from hydrocolloid or poor in hydrocolloid, and such zones may advantageously form the outer zone and/or inner zone; but may additionally be partition zones within a hydrocolloid-containing self-adhesive elastomer mass.

A long series of other materials may form parts of the product according to the invention, either as separate zones or as parts of zones containing an adhesive. As examples may be mentioned that one or more kinds of zones expediently may consist of a foam material having open or closed cells. In the foam material a biologically active substance may be present, for instance a medicament or an antiseptic or antibiotic. The biologically active substance may be present within the cells of a foam with open cells or be present in the very foam material, i.e. as a component of the walls of open or closed cells which for instance may consist of a foamed gel material such as gelatin.

Biologically active substances may also be present in other materials than foam materials. For instance one or more zones of material may comprise hydrophilic gel substance containing an agent effective against warts, e.g. cantharidine, salicylic acid, silver nitrate, podophyllin, or an anti-metabolitic cytostatic such as cytarabine, fluorouracil or mercapto-purine.

One or more zones of the product may be made from a hydrophilic gel substance containing one or more keratolytically active substances, for instance carbamide, salicylic acid and/or lactic acid.

Furthermore, one or more zones may for instance contain one or more compounds inhibiting mitosis, e.g. anthracene, silver nitrate or glucocorticoids such as mildly, medium strongly or strongly active corticosteroids such as hydrocortisone, triamcinolone acetonide or betametasone.

The gel substances mentioned above may be hydrophilic or hydrophobic, optionally of a desired HL-balance (hydrophilic-lipophilic balance), and optionally a supporting structure may be incorporated therein in the form of a foam of, e.g., a polyether, collagen or gelatin, or in the form of fibres, filaments or woven or nonwoven textile material, e.g. of a polyester or cotton. Hydrophilic gels may for instance be mixtures of karaya and glycerol; of pectin, lower molecular weight polyethylene glycol and glycerol; or mixtures of gelatin, glycerol and water.

Hydrophobic gels may for instance consist of mixtures of styrene-isoprene-styrene blockcopolymers and paraffin; mixtures of styrene-isoprene-styrene blockcopolymers, liquid paraffin and dioctyladipate; or mixtures of nitrocellulose, ricinus oil and rosin.

As examples of active substances which may be incorporated into the gel substances may be further mentioned antiseptics such as iodophors, silver compounds, hexidine or chlorohexamine; vitamins; and antibiotics, wound-healing agents and growth-promoting substances.

Foam materials which may be present as a special kind of zone or form a supporting structure in the gel substances just mentioned, may for instance be of a polyether, polyethylene, polyvinyl chloride, gelatin or collagen.

The skin barrier product according to the invention may further comprise liquid-transporting structures. They may for instances be fibres, filaments or woven or nonwoven textiles; and optionally tubular structures may be present in the form of capillaries or bodies having ducts, the capillaries or ducts being substantially at right angles to the surfaces of the skin barrier product. Bodies containing ducts may for instance be of plastics or rubber-like materials.

The skin barrier product may also incorporate layers with so-called superabsorbing materials; such materials are well-known in connection with absorption products such as sanitary towels and diapers.

According to a special embodiment of the skin barrier product it comprises zones or strands of (a) a self-adhesive material preferably without hydrocolloid and (b) a hydrophilic, electrically conductive gel substance, optionally separated by an aluminium foil. This embodiment is especially suitable for the production of electrodes for use in transneurocutaneous stimulation (TNS). Contrary to electrodes for electrocardiographs, which transmit specific voltage differences, the TNS-electrodes should only be electrically conductive and this is achieved by means of the conductive gel substance which is preferably the more structure-forming component in this embodiment. It possesses the advantage of utilizing self-adhesive technology proper so that an electrode manufactured therefrom because of the self-adhesive zones may be fixed in a given position for many days.

The electrially conductive gel may be a hydrophilic basal polymer such as polyacrylamide, salts of polymethacrylic and polyacrylic acids, polyvinyl alcohol or Na-CMC, softened by means of an emollient of low viscosists, e.g. a liquid polyol such as glycerol and optionally with an addition of typically 0.1–1.5% of NaCl, KCl or another biologically harmless, readily soluble salt and if desired 1–10% of water.

A product of this kind is preferably made from a stack of alternating sheets or lengths rather them from strands. The zones in the finished product of the invention may be straight, curved or wavy, but may especially be approximately circular. In that case, the product may be made from a stack as alternating layers in the same manner as described in connection with the annular products, only omitting the aperture in the middle. The production may be performed in analogy with that described for the annular products.

BRIEF DESCRIPTION OF THE DRAWINGS

In the following the skin barrier product according to the invention will be described more fully with reference to the drawing. In the drawing

DETAILED DESCRIPTION OF SOME EMBODIMENTS

Figure 1:
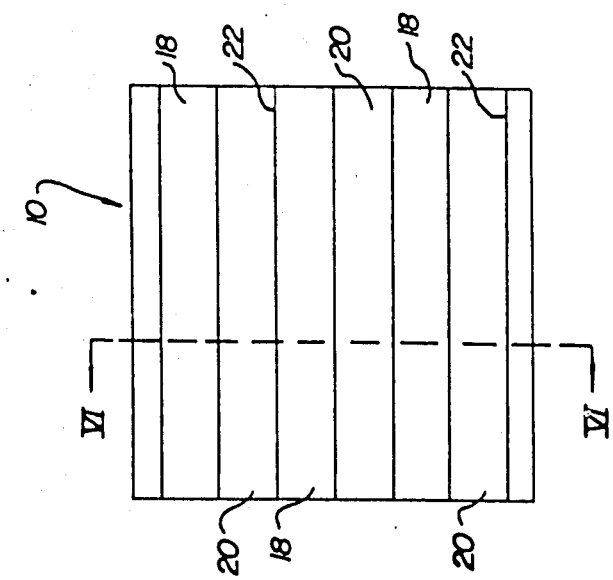
Figure 6:
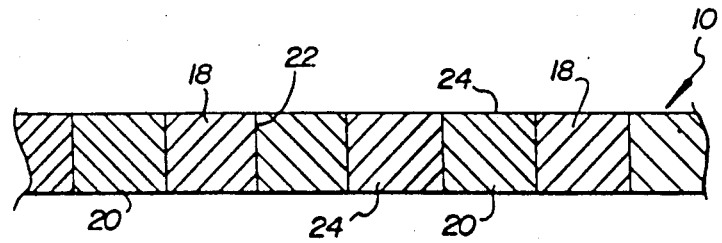

FIGS. 1 and 6 show a skin care product 10 consisting of alternating strips or zones 18 and 20 of material, all extending in a direction substantially perpendicular to the surfaces of the product. They are shown as flat, rectilinear strips but might for instance be curved or wavy. As shown they are also substantially parallel, which here as in other parts of the specification means that the individual layers have substantially equidistant boundary surfaces or edges 22.

The zones 18 consist of an agent adhesive to the skin and comprising hydrophilic components, especially of the kind consisting of a continuous phase containing a self-adhesive elastomer mass and one or more hydrocolloids dispersed therein as a discontinuous phase. The zones 20 consist of a continuous phase of a self-adhesive elastomer mass, preferably of the same kind as in the zones 18, but without any hydrophilic discontinuous phase. Thus the zones 20 will act as barriers which to a high degree will counteract migration of aqueous liquids from the zones 18 to the zones 20. The zones 20 do not, or only to a small degree, absorb water from the skin or wound surface to which a finished product produced from this semi-manufacture is attached.

The skin care product shown in FIGS. 1 and 6 may be produced by alternately joining long strips of material 18 and material 20 to form a block which is subjected to light pressure to ensure full contact between the surfaces of the layers, after which the block is sliced into pads having a thickness of, e.g., 0.5–2 mm. It is expedient that the widths and numbers of the strips correspond to the desired surface dimensions of the product. It is observed that the thickness dimension shown in FIG. 6 is not necessarily correct relative to the length dimension. The lines 24 in FIG. 6 mark surfaces, but might as well represent detachable protective covers, for instance of siliconized paper, which may be placed on the semi-manufacture before it is worked up to form a final product.

Slicing of the block of layers 18,20 may be carried out with a cutting wire but preferably takes place with a knife the sides of which are constantly moistened with a solvent which does not affect the materials of the block and which evaporates rapidly after the cutting. When the skin adhesive is one of the kinds described in the U.S. Pat. Nos. 4,231,369 and 4,367,732 ethanol or isopropanol is preferably used as the solvent.

Figure 2:
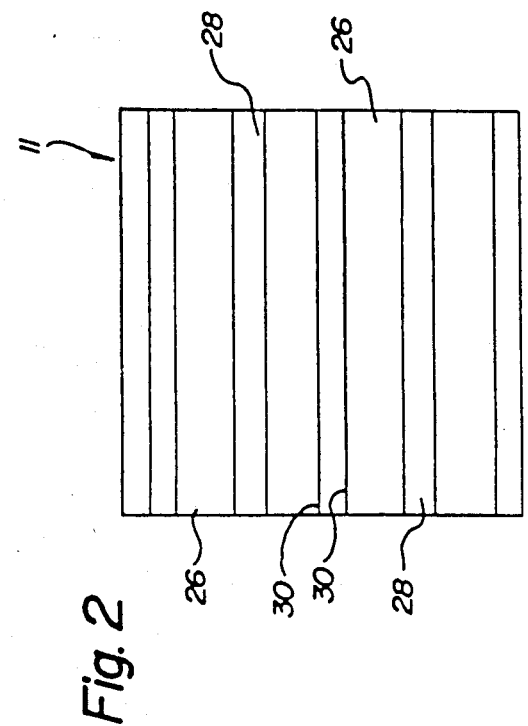
FIGS. 1–5 show cuttings from five different embodiments of the product according to the invention, seen from the surfaces thereof, FIG. 6 in larger scale shows a section along the line VI—VI in FIG. 1 (in principle even a partial section of FIG. 9), FIG. 7 a similar section as FIG. 6, but of the embodiment according to FIG. 2, and FIGS. 8–9 two different embodiments of the skin barrier product according to the invention and suitable for use in securing an ostomy pouch and seen from the surface.
Figure 7:
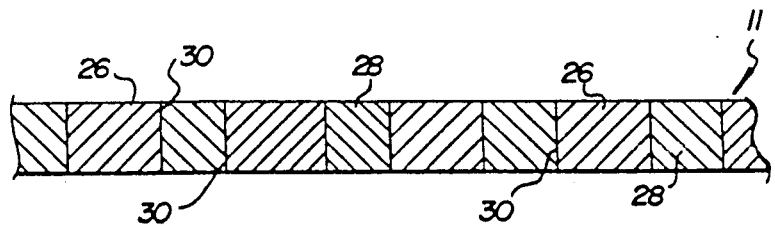

FIGS. 2 and 7 show a skin barrier product 11 also built up from parallel, rectilinear thin zones 26 and 28. The zones are of different widths and can optionally be separated by barriers of foil 30. The zones 26 consist of a skin adhesive material of for instance the same kind as the zones 18 or 20 in FIG. 1. The zones 28 consist of or contain a material active in some desired respect, here exemplified by an electrically conductive, hydrophilic gel material; in that case the zones of elastomer mass 26 preferably do not contain hydrophilic components and the barriers of foil 30 are preferably of aluminium. The electrically conductive material may for instance consist of karaya, glycerol, propylene glycol, NaCl and water in the weight ratio 42:53:3:0.25:3; or polyacrylate, glycerol, water and NaCl in the weight ratio 62:36:2:0.15; or polyoxyethylene, propylene glycol, water NaCl and KCl in the weight ratio 11:45.5:43:0.45:0.05; or gelatin, glycerol, water and NaCl in the weight ratio 47:47:4.8:1.2.

Figure 3:
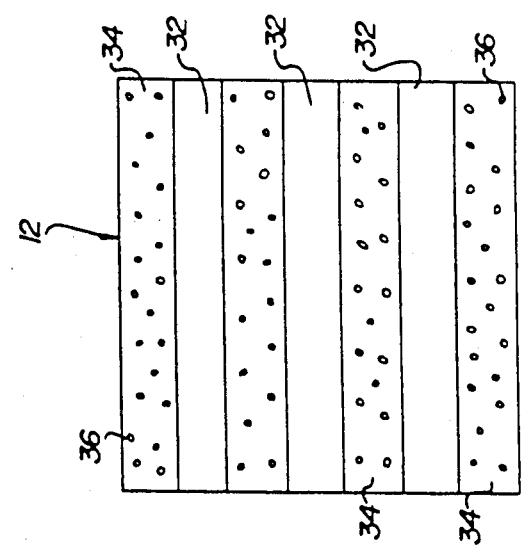

The skin care product 12 shown in FIG. 3 consists of two alternating kinds of zones of material, viz. zones 32 of a skin adhesive, for instance of the same kind as the zones 18 in FIG. 1, and zones 34 of a material particularly suitable for transporting liquid through the thickness dimension of the product, viz. perpendicular to the plane of the paper. The structure permitting the transportation is shown as capillaries 36 but the transportation capacity may also be caused by, e.g., an open-cell foam material constituting or forming part of the zones. The capillaries may be incorporated into a hydrocolloid-free skin adhesive of, e.g., the same kind as the adhesive in zones 20 in FIG. 1 so that liquid will not migrate in the surface direction of the product. This product is especially suitable for the production of dressings for suppurating wounds. Migration of liquids parallelly to the surfaces may also be prevented by impermeable barrier layers, for instance foils between layers 32 and 34.

The products shown in FIGS. 2 and 3 may be produced in the same way as that shown in FIG. 1.

Figure 4:
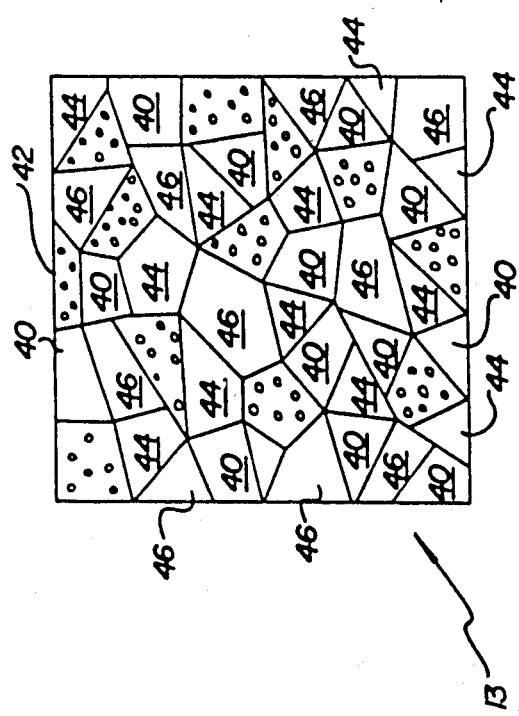

On the other hand, FIG. 4 shows a skin care product 13 built up and produced in another way. Its zones are short prismatic strands 40,42,44,46 extending in a direction intersecting the surface of the product and being of two or more different kinds. Such a product is produced by extruding long strands of the respective kinds of material through nozzles, then preferably through a funnel-shaped tube in order to ensure that there will be no airfilled interstices between the strands, and subsequent slicing of the composite strand thus formed into thin pads. It will be understood that the final semi-manufacture will not have planar boundary surfaces between the strands as shown for the sake of clearness. Instead of being prismatic the nozzles may be round and of identical or different sizes, just as the prismatic strands may all have the same size and may advantageously have the cross-section as equilateral triangles, squares or regular hexagons. The slicing preferably is carried out at right angles to the longitudinal dimension of the long strands but might be oblique thereto.

In the product shown in FIG. 4 the strands 40 of skin adhesive are of the same kind as are the zones 18 in FIG. 1; the strands 42 are liquid-transporting as are the zones 34 in FIG. 3, preferably with capillaries embedded in a hydrocolloid-free skin adhesive; the strands 44 consist of a hydrocolloid-free adhesive like the zones 20 in FIG. 1; and the strands 46 contain a substance biologically active in skin care, e.g. an antiseptic or antibiotic, a growth-promoting agent or a wound-healing agent.

Figure 5:
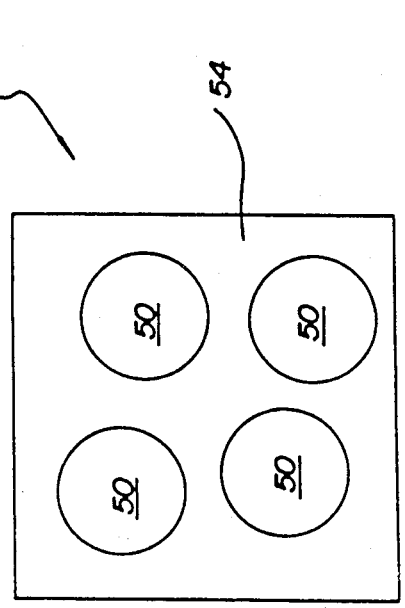

The skin care product 14 shown in FIG. 5 contains a plurality of comparatively wide circular-cylindrical strands 50 of a skin adhesive of the same kind as that of the zones 18 in FIG. 1, viz. a self-adhesive elastomer mass containing a hydrocolloid embedded in a common strand 54 consisting of a skin adhesive of the same kind as that in the zones 20 in FIG. 1, i.e. without a hydrocolloid or with a low content of hydrocolloid.

This product may be produced by extrusion through a nozzle for the material for the strand 54 containing channels through which the material for the strands 50 is conveyed.

It will be appreciated that the strands referred to in FIG. 4 and 5 are quite short, i.e. as the thickness of the product.

Figure 8:
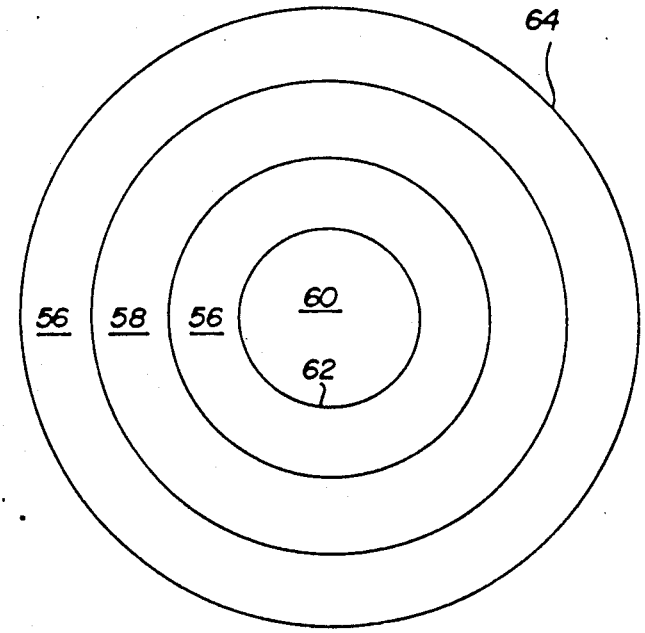

FIG. 8 shows an annular skin barrier product for use in the production of ostomy appliances. It consists of three annular zones of material, outer and inner zones 56 of a skin adhesive of for instance the same hydrocolloid-containing kinds as the material of the zones 18 in FIG. 1, and therebetween a hydrocolloid-free zone 58. Inside the inner zone 56 there is an aperture 60, and penetration of liquids from said aperture to the inner zone of sealing agent 56 is prevented by a cover of liquid-tight film or foil 62; the entire annular product is encased in a corresponding liquid-barrier 64.

The number of annular zones may be greater, and annular zones consisting of or comprising other materials may also be present, e.g., liquid-transporting zones or zones containing biologically active substances.

An annular product as shown in FIG. 8 may be produced by co-extrusion and slicing.

Figure 9:
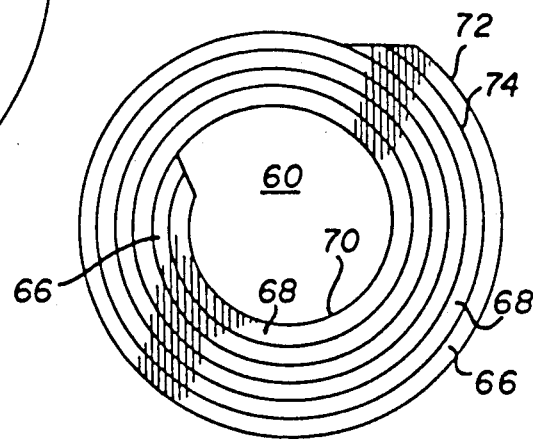

Another embodiment of an annular skin barrier product is shown in FIG. 9. The zones of material here are in the form of layers 66,68 of Archimedean spirals surrounding a central aperture 60. There are two such "co-current" spirals extending from an inner end to an outer, but there might be more. One of the spirals 66,68 consists of a hydrocolloid-containing adhesive as that in the layer 18 in FIG. 1, the other of a hydrocolloid-free material of the same kind as that in the layer 20 in FIG. 1. Innermost adjacent the aperture 60 and outermost facing the outer world a barrier foil or film as the foils or film 62,64 in FIG. 8 may be provided.

This product may be produced by uniting two wide lengths corresponding to the zones 66 and 68, optionally providing the laminate thus formed with barrier foil or film on one side, and winding them around a suitable cylindrical object on which the roll may slide. Then the roll is moved forward in its length direction (the width direction of the lengths) and is sliced into thin pads just in front of cylindrical core. It will be understood that the ring formed may nave a barrier foil for every two layers, seen radially. The line 74, however, only marks the boundary surface between the two spirals, but might also represent a barrier foil.

By producing blanks for sealing rings for ostomy pouches as explained in connection with FIG. 8 and FIG. 9 there is achieved the advantage of avoiding the waste of material that will inevitably occur in the known production of such sealing rings by punching from sheets or lengths of the skin adhesive.

By rolling into spirals and slicing, an electrically conductive skin barrier product may be advantageously produced. In that case one of the layers of material 66,68 consists of a self-adhesive elastomer mass mainly of hydrophilic components, and the other of an electrically conductive, hydrophilic gel material as described hereinbefore. A thin aluminium foil may further be placed between the lengths of material.

In order to prevent flow of the edges the skin barrier products described may be bevelled along their edges as described in European patent application publication No. 264,299.

EXPERIMENTS

In the field of ostomy bandages the so-called two-piece bandages gain an increasing popularity, i.e. for economic reasons because it is possible to change and discard the parts at different frequencies.

In two-piece ostomy equipment an ostomy bag or ostomy stopper is firmly attached to one member of an annular two-part coupling ring and a skin barrier and sometimes also other equipment firmly attached to the other. The rings can be hermetically united to each other by some snap-like closing structure and comparatively easily disjoined from each other. Thus, during function the skin barrier keeps the bag or stopper in place around or in the ostomy opening. Numerous examples of such ring coupling systems are known, e.g. from European patent application publication No. 188,776 (FIG. 7) and Danish patent specification No. 151,044 corresponding to U.S. patent application Ser. No. 987,523 of May 27, 1986.

In such two-piece systems the part with the ostomy bag or stopper must necessarily be discarded and replaced frequently, commonly several times a day, whereas there is no reason to replace the skin barrier with its coupling ring as long as the skin barrier itself is intact.

Adhesive materials as those described in the introducing parts of the present specification and disclosed in, i.a. U.S. Pat. Nos. 3,339,546, 4,321,369 and 4,367,632, normally function excellently for periods of one to two days, but during the period following that the juices escaping from the ostomy opening will usually penetrate into the skin barrier and cause it to leak, which is very unpleasant for the user of the ostomy closing system.

By experiments it has been shown that a skin barrier according to the present invention will greatly prolong the lifetime of the coupling part provided with the skin barrier and belonging to a two-piece ostomy system.

A. 1. An adhesive mass as described in the Example of U.S. Pat. No. 4,367,632 applied as a melt to a thickness of 1 mm on siliconized paper and a film of EVA (ethylene-vinylacetate copolymer) having a thickness of 70 μm was laminated onto its free surface. From this there was in the usual manner punched circular discs having an outer diameter of 100 mm and varying inner diameters (25 to 50 mm, individually adapted to the sizes of the stomas of the volunteers participating in the tests). The center parts and the material between the discs were discarded as waste material.

A. 2. The same kind of adhesive mass as above was applied as a melt to a thickness of 1.5 mm to a length of siliconized paper. Another adhesive mass, having the same composition as the first one except for its content of hydrocolloid (30% Na-CMC) was applied as a melt to a thickness of 0.5 mm onto another length of siliconized paper.

The two lengths, each having a width of 1 meter, were wound together, the surfaces not provided with the siliconized paper facing each other, while pulling the siliconized papers off. In this manner there was formed 1 m long cylinders having an outer diameter of 100 mm; the winding was made around re-usuable cylindrical, silicone -coated rods of varying diameters (25-50 mm) to accommodate various sizes of stomas. The result was a spirally coiled roll having a cross-section largely as the disc shown in FIG. 9 of this specification. The layers of the roll alternated throughout its thickness between layers with and layers without hydrocolloid in the adhesive mass.

The roll was sliced into annular discs each having a thickness of 1 mm by the aid of a specially designed slicing machine with a rotating steel blade which was constantly moistened with ethanol from a felt pad. The machine could cut 60 such discs per minute.

The machine was adapted to catch the thin, flexible discs formed (which each is a skin barrier product according to the invention on a sheet or length of EVA film which may serve as a carrier or packing material for the product or may even be a part of an ultimate product produced from the semi-manufacture.

It should be noted that the hydrocolloid-containing adhesive mass lost its self-adhesive properties in the surface immediately upon the cutting operation because the particles of hydrocolloid appeared in the very surface. After storage, however, the material regained its surface self-adhesive properties. The 0.5 mm zones of hydrocolloid-free adhesive mass sufficed to permit the immediate adhering to the EVA film and other suitable surfaces.

A. 3. Thereafter both types of skin barrier, 1 and 2, were worked up with a ring coupling to form a stopper system as illustrated by FIG. 7 in European patent application publication 188,776 (Danish patent specification No. 153,122).

The two stopper systems were comparatively tested by 25 colostomy patients who were users of such stopper systems.

A significant difference was found between the two different kinds of skin barriers. Skin barriers No. 1, that comprising only the hydrocolloid-containing adhesive, could be used in average only approximately 2 days, whereas skin barrier No. 2, that comprising alternating zones of hydrocolloid-containing and hydrocolloid-free adhesive could be used in average about 10 days.

B. Another experiment was made with 20 volunteers who were accustomed to using ileostomi bags attached to the body by the aid of a skin barrier according to A. 1. above.

The test skin barriers were made to dimensions as described under A.2. above, but with alternating zones, viz. 1 mm wide zones of a hydrocolloid-free adhesive mass as described under A.2., alternating with non-self-adhesive zones (3 mm wide) of gelled karaya/glycerol 1:1.

The preparation took place in analogy to what is described in U.S. Pat. No. 4,062,261 (DK 132,645), only with the difference that the elastomer mixture there shown was replaced by the abovementioned self-adhesive mass. In this process the sheet material, having a width of 1 meter, only had to be wound alone while at the same time removing a single sheet of siliconized paper.

The skin barrier product was confectioned as described under A., and tested by use in a two-piece bag system with an ileostomy bag mounted by the aid of a two-piece coupling.

Again, there was found an outspoken improvement of the lifetime of the skin barrier in comparison with that of the usual skin barrier. Moreover, the users much appreciated the presence of karaya which is known as an extremely skin-friendly material but which suffers from the inconveniency that it disintegrates too quickly.

INDUSTRIAL USE OF THE INVENTION

It is expected that the invention will attain an almost immediate use in the manufacture of skin barriers for attaching ostomy equipment, drains and catheters to the human body; and later also in highly specialized skin and wound care products.

What is claimed is:

1. In an adhesive, flat skin barrier product having a flat surface adapted to come into contact with the skin and an opposite flat surface, for use as a semimanufacture in the production of dressings, skin-and wound-care devices, electrodes for application to the skin, fastening means for dressings, ostomy equipment, wound drains and catheters, the improvement wherein said product consists of a plurality of alternating zones of at least two different kinds of material, at least one kind of material consisting of a substantially non-allergenic self-adhesive material, the zones of material extending substantially parallelly through the entire thickness of the product in a direction intersecting its flat surfaces wherein within a given zone the composition of said material is substantially uniform.

2. A skin barrier product according to claim 1, wherein the zones of material extend substantially at right angles to the flat surfaces of the product, from the surface adapted to contact the skin to the opposite surface, and hence are of a length substantially the same as the thickness of the product.

3. A skin barrier product according to claim 1, wherein at least one zone is entirely surrounded at all edges by one other zone.

4. A skin barrier product according to claim 1, wherein at least two kinds of material have been wound together to form neighbouring zones each substantially in the form of an Archimedean spiral.

5. A skin barrier product according to claim 1, wherein the zones of material, when seen from the surface of the product adapted to contact the skin, each have a shape selected from rectilinear, curved and wavy, which are substantially parallel and all extend from one edge of the product to another.

6. A skin barrier product according to claim 5 wherein, at least one zone of material has a function other than an adhesive function.

7. A skin barrier product according to claim 1, wherein at least one zone is entirely surrounded by a multiplicity of other zones.

8. A skin barrier product according to any of claims 1-6 and 7 wherein at least one kind of zone consists of a self-adhesive material comprising a continuous phase containing a self-adhesive elastomer mass and at least one hydrocolloid which is at least water swellable substantially evenly distributed as a discontinuous phase in the continuous phase.

9. A skin barrier product according to claim 1 wherein the units of material are substantially parallel alternating strips of identical or different widths.

10. A skin barrier product according to one of claim 1 or claim 2, wherein at least one kind of zone consists of a material which at least hampers the migration of solid, liquid and gaseous substances to and from neighbouring self-adhesive zones.

11. A skin barrier product according to claim 10, wherein said zone consists of a material which at least hampers the migration of aqueous liquids to neighbouring hydrocolloid-containing self-adhesive materials.

12. A skin barrier product according to claim 11, wherein the material at least hampering the migration of solid liquid and gaseous substances is hydrophobic and ductile under the influence of small forces and contains a self-adhesive elastomer mass but no hydrocolloid.

13. A skin barrier product according to claim 11, wherein the zones at least hampering the migration of solid, liquid and gaseous substances are at least one of films or foils of at least one of plastic, metal or laminates thereof.

14. A skin barrier product according to any one of claim 1, claim 2 or claim 7, wherein each zone of material is a short strand extending from the flat surface adapted to contact the skin to the opposite flat surface and each strand has a cross-sectional shape and size, when viewed in a plane parallel to said flat surfaces, such that a multiplicity of such strands together substantially fill up the product.

15. A skin barrier product according to any one of claims 1, 2 or 3 comprising a continuous phase containing a self-adhesive elastomer and at least one hydrocolloid which is at least water swellable and is substantially evenly distributed therein as a discontinuous phase; and a plurality of strands of a different material variously disposed through said continuous phase and extending from the flat surface adapted to contact the skin to the opposite surface, said self adhesive material substantially filling up the interstices between said strands.

16. A skin barrier product according to claim 1 in the form of a blank for the production of an annular pad for attaching drains, ostomy pouches or other equipment to a mammal body, wherein the alternating zones of material are co-axially cylindrical, and in that the product is provided with a central aperture.

17. A skin barrier product according to claim 16, wherein said blank is provided on its outer edge and its inner edge with a water-impermeable barrier layer.

18. A skin barrier product according to claim 1 wherein at least one of the kinds of zones contains one or more biologically active substances.

19. A skin barrier product according to claim 18, wherein said biologically active substance is selected from the group consisting of substances effective against warts, keratolytically active substances and mitosis-hampering compounds.

20. A skin barrier product according to claim 1 wherein at least one kind of zone possesses the property of transporting liquids in the thickness direction of the product.

21. A skin barrier product according to claim 1 wherein at least one zone consists of a self-adhesive material without a hydrocolloid and at least one zone consists of an electrically conductive hydrophilic gel substance.

22. A skin barrier product as defined in claim 8 wherein said hydrocolloid is water soluble.

23. A skin barrier product according to claim 1, wherein the zones of material are substantially alternating strips.

24. A skin barrier product as defined in claim 15 wherein said hydrocolloid is water soluble.

25. A skin barrier product according to claim 1 in the form of a blank for the production of an annular pad for attaching drains, ostomy pouches and other equipment to a mammal body, wherein the alternating zones of material form an Archimedean spiral, and in that the product is provided with a central aperture.

26. A skin barrier product according to claim 1 in the form of a blank for the production of an annular pad for attaching drains, ostomy pouches and other equipment to a mammal body, wherein the alternating zones of material are coaxial and cylindrical and surround a central aperture.

27. A skin barrier product according to any one of claims 1, 2 or 3, comprising a plurality of strands composed of a self-adhesive material comprising a continuous phase containing a self-adhesive elastomer and at least one hydrocolloid which is at least water-swellable and is substantially evenly distributed therein as a discontinuous phase, said plurality of strands extending from the flat surface adapted to contact the skin to the opposite surface and being embedded in a different material filling up the remainder of the skin barrier product.

28. A skin barrier product according to claim 26, wherein said blank is provided on its outer edge and its inner edge with a water-impermeable barrier layer.

* * * * *